United States Patent
Weyl

(10) Patent No.: US 7,136,539 B2
(45) Date of Patent: Nov. 14, 2006

(54) DRUG SAMPLE IDENTIFICATION PERIPHERAL

(76) Inventor: John A. Weyl, 42 W. Buffalo St., Churchville, NY (US) 14428

( * ) Notice: Subject to any disclaimer, the term of this patent is extended or adjusted under 35 U.S.C. 154(b) by 627 days.

(21) Appl. No.: 10/202,923

(22) Filed: Jul. 25, 2002

(65) Prior Publication Data

US 2003/0021454 A1   Jan. 30, 2003

Related U.S. Application Data

(60) Provisional application No. 60/307,919, filed on Jul. 26, 2001.

(51) Int. Cl.
*G06K 9/36* (2006.01)
(52) U.S. Cl. .................. 382/280; 382/274; 378/43
(58) Field of Classification Search ............. 382/100, 382/103, 128–134, 141, 157, 165, 169, 170, 382/172, 180, 181, 191, 203, 207, 216, 232, 382/274, 305, 280–289; 705/2; 702/128; 340/568.1; 600/425; 235/462.01; 378/43
See application file for complete search history.

(56) References Cited

U.S. PATENT DOCUMENTS

| 4,945,476 | A | | 7/1990 | Bodick et al. |
| 5,605,153 | A | * | 2/1997 | Fujioka et al. ............ 600/425 |
| 6,108,635 | A | * | 8/2000 | Herren et al. ................ 705/2 |
| 6,260,021 | B1 | * | 7/2001 | Wong et al. ................. 705/2 |
| 6,272,469 | B1 | * | 8/2001 | Koritzinsky et al. ......... 705/2 |
| 6,543,692 | B1 | * | 4/2003 | Nellhaus et al. ....... 235/462.01 |
| 6,574,580 | B1 | * | 6/2003 | Hamilton ................... 702/128 |
| 6,707,381 | B1 | * | 3/2004 | Maloney ................ 340/568.1 |
| 6,711,283 | B1 | * | 3/2004 | Soenksen .................. 382/133 |

* cited by examiner

*Primary Examiner*—Jingge Wu
*Assistant Examiner*—Seyed Azarian
(74) *Attorney, Agent, or Firm*—Basch & Nickerson LLP

(57) ABSTRACT

The present invention is a method and apparatus for drug sample identification, including a scale for weighing a drug sample and an imaging module for capturing digital images of the drug sample, from at least two different visual perspectives simultaneously, and an transmitting the collected data and images, via an interface, to a computer for storage and association with an image database.

21 Claims, 5 Drawing Sheets

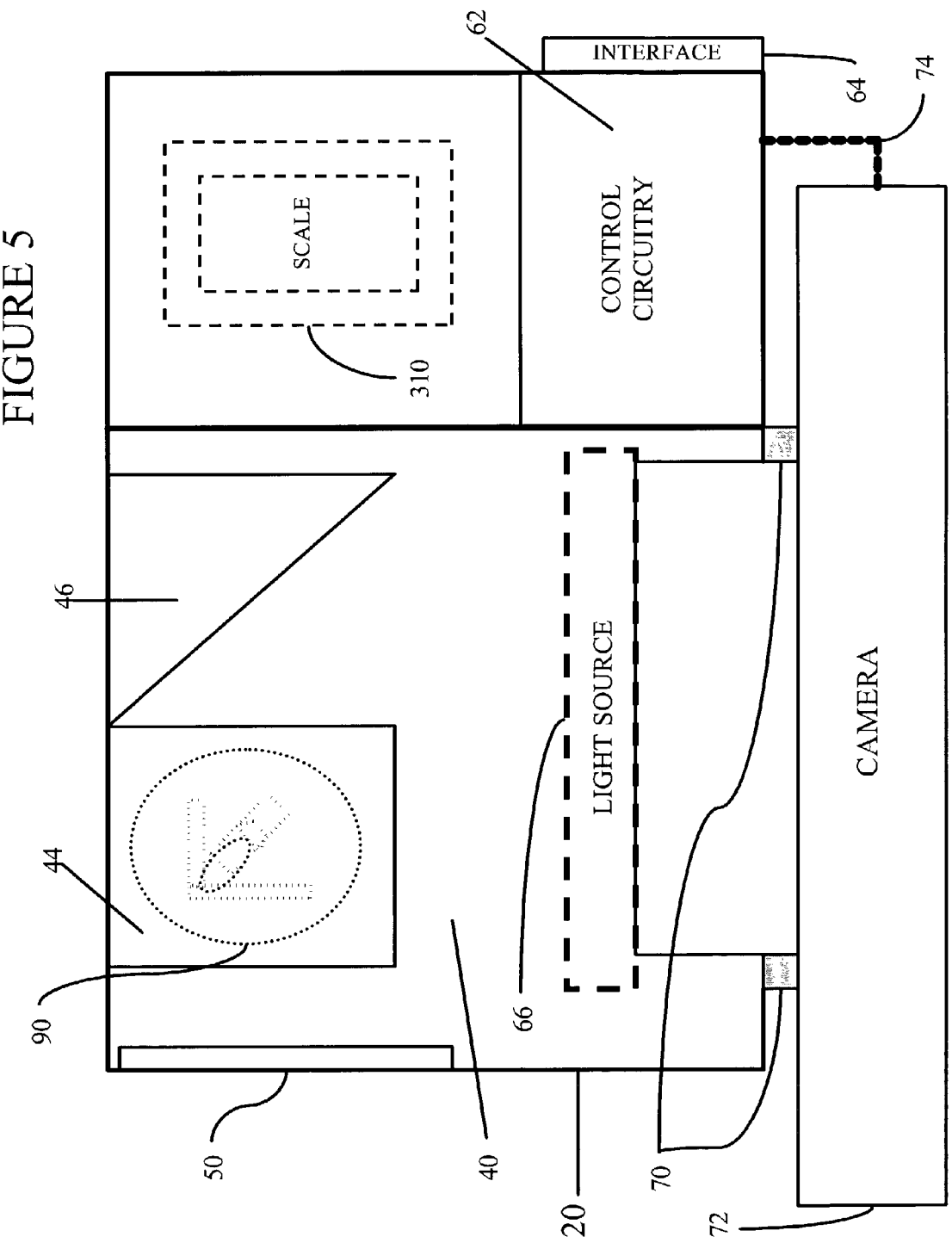

DRUG SAMPLE IDENTIFICATION PERIPHERAL

PRIORITY INFORMATION

This application claims priority from U.S. Provisional Patent Application, Ser. No. 60/307,919, filed on Jul. 26, 2001; the entire contents of which are hereby incorporated by reference.

CROSS REFERENCE

The following related co-pending U.S. patent application is hereby incorporated by reference for its teachings "System and Method To Aid Diagnoses Using Cross-Referenced Knowledge and Image Databases," U.S. patent application Ser. No. 09/919,275 was filed on Jul. 31, 2001.

FIELD OF THE PRESENT INVENTION

The present invention relates generally to the identification of oral pharmaceuticals such as pills, and including illegal street drugs, and more particularly the present invention relates to a device, operatively associated with a programmable computing device, to obtain visual and other physical information about such pharmaceuticals.

BACKGROUND OF THE PRESENT INVENTION

In the "war on drugs" being waged in and by the U.S. and other countries, one difficulty in waging the war is the collection and dissemination of data relating to new drugs or new drug forms made available on the street, and the manner in which such drugs are spread or distributed. In most circumstances, there is a considerable time delay (e.g., days, weeks, or even months) before the law enforcement and medical communities are able to identify and characterize new drugs (new in content, potency, size, shape, color, etc.) so as to begin the process of enforcement and/or treatment.

Moreover, even when such information is or becomes available, it is sometimes only partially complete, lacking in detail to enable easy dissemination to the communities that need it, such as drug enforcement agents, local law enforcement personnel, emergency room personnel, and clinic personnel.

Therefore, it is desirable to provide a device that can quickly collect and disseminate detail data relating to new drugs or new drug forms. It is also desirable to provide a device that can quickly collect and disseminate detail data relating to the manner in which such drugs are spread or distributed. It is further desirable to provide a device that can quickly collect and disseminate detail data relating to new drugs or new drug forms and detail data relating to the manner in which such drugs are spread or distributed, which is portable. Lastly, it desirable to provide a device that, without significant effort, generates a standardized set of characteristics and associated images that is useful in the identification of new drugs or new drug forms.

SUMMARY OF THE PRESENT INVENTION

One aspect of the present invention is a drug sample identification system. The drug sample identification system includes an imaging staging module to enable a capturing of an image of the drug sample from at least two different visual perspectives simultaneously.

Another aspect of the present invention is a method for identifying a drug sample. The method places a drug sample in an imaging stage module and captures of an image of the drug sample from at least two different visual perspectives simultaneously.

BRIEF DESCRIPTION OF THE DRAWINGS

FIG. 5 is a block diagram of another embodiment of a drug sample ID peripheral according to the concepts of the present invention.

DESCRIPTION OF THE PREFERRED EMBODIMENT

Figure 1:
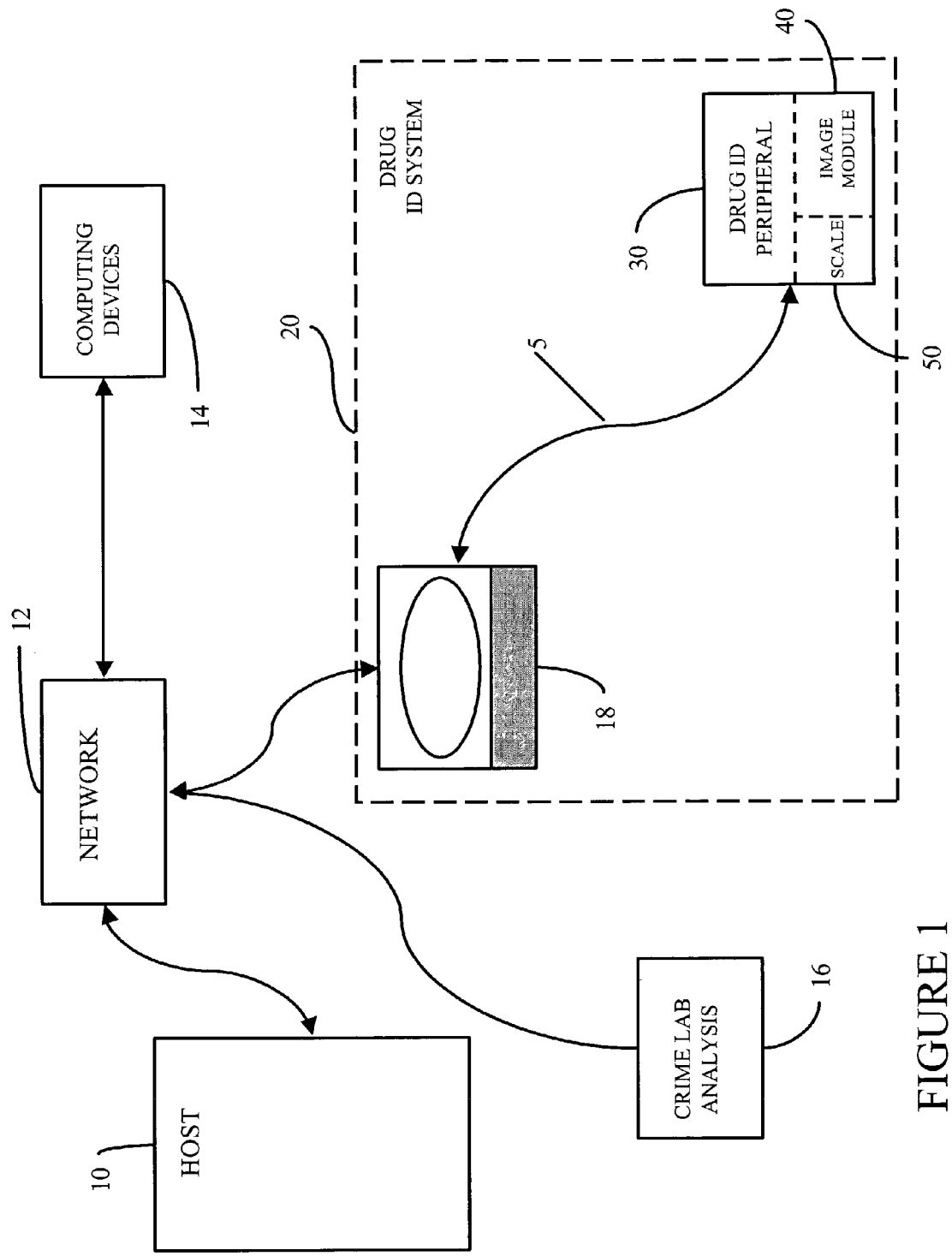
FIG. 1 is a schematic block diagram of a drug sample identification system and its role in an overall drug analysis system according to the concepts of the present invention.

The present invention will be described in connection with preferred embodiment however, it will be understood that there is no intent to limit the invention to the embodiments described. On the contrary, the intent is to cover all alternatives, modifications, and equivalents as may be included within the spirit and scope of the invention as defined by the appended claims.

For a general understanding of the present invention, reference is made to the drawings. In the drawings, like reference have been used throughout to designate identical or equivalent elements. In describing the present invention, the following term(s) have been used in the description.

An "image" is a pattern of physical light that is both directly or reflectively received by a device suitable for creating a digital representation of the intensity and/or color of the physical light. An "image set" is a set of one or more images. An image may be divided into "segments," each of which is itself an image. A segment of an image may be of any size up to and including the whole image.

Each location in an image may be called a "pixel." A "pixel" is the smallest segment of an image whose value is indicated in an item of data defining the image. In an array defining an image in which each item of data provides a value, each value indicating the color of a location may be called a "pixel value". Each pixel value is a bit in a "binary form" of an image, a gray scale value in a "gray scale form" of an image, or a set of color space coordinates in a "color coordinate form" of an image, the binary form, gray scale form, and color coordinate form each being a two-dimensional array defining an image.

An "imaging device", such as an aspect or embodiment of the present invention, is a device that can receive an image and provide an item of data defining a version of the image.

A "digital camera" is a device that can receive an image and provide an item of data defining a version of the image An "image output device" is a device that can receive an item of data defining an image and provide the image as output.

A "display" is an image output device that provides the output image in human viewable form. The visible pattern presented by a display is a "displayed image" or simply "image".

A "computing device" is a device capable of processing digital information. Such computing devices may be personal computers ("PC"), laptops, personal digital assistants ("PDA"), a mainframe computer, or other electronic device that performs digital processing upon digital data.

A "network" is a communication system allowing computing devices to communicate therebetween, transfer data therebetween, etc. Examples of such systems may include a local area network ("LAN"), a wide area network ("WAN"), or the Internet.

As illustrated in FIG. 1, an overall drug identification/analysis system may include a host computer or mainframe 10 which stores drug information in a database, preferably associated with a computer program and image database, that can be accessed through a network 12 by other computing devices 14 and a crime analysis lab computer system 16. Furthermore, the drug sample identification system 20 of the present invention can be in communication with the host computer 10 through the network 12.

The drug sample identification system 20 of the present invention may include a computing device 18, which may be a personal computer, a laptop, a personal digital assistant, or other electronic device that performs digital processing upon digital data. The computing device 18 may be connected to drug sample identification peripheral 30 through a communication channel 5. The communication channel 5 between the computing device 18 and the drug sample identification peripheral 30 may be a hardwired connection; such as, a parallel cable connection, a serial cable connection, or a universal serial bus cable connection; an infrared connection, or a wireless connection.

As noted above, computing device 18, which may be connected to the drug sample identification peripheral 30 through a communication channel 5, includes a computing platform as well as a visual interface in the form of a display, and thereby may provide control functionality for the system via a pre-programmed set of instructions stored in memory (not shown).

In the embodiment depicted in FIG. 1, the drug sample identification system 20 is connected to a network 12, via a wired or wireless connection, for the purpose of uploading the drug sample data to a host 10, and where the drug sample data may be subsequently disseminated to a plurality of networked computing devices 14 and 18. Such a connection may be established whenever computing device 18 is in use, or on a regular schedule. Connection with host 10 would facilitate the exchange of information with a master database, of which all or a portion thereof may be replicated in computing device 18 to enable its use.

The drug sample identification peripheral 30 may, according to the concepts of the present invention, include an imaging module 40 and a scale 50.

The drug sample identification peripheral 30 may also include any necessary circuitry to control its operations and to effectively transmit information to the computing device 18, as well as, to receive information therefrom. The circuitry may include a control board, central processing unit, or other control/logic unit to control the functions and operations of the imaging module, the scale, and interface. The circuitry module may also include a memory, a power supply, and/or communication circuitry. The power supply may be a battery or rechargeable battery. The power supply may also include an AC to DC adapter.

The drug sample identification system 20 may be used to confirm the identification of a drug sample based upon physical and visual characteristics, where such characteristics of the drug sample and similar characteristics for at least one known drug may be displayed to a user to make a comparison and confirm an identification of the drug sample. Moreover, it is possible that some or all of the initial sampling, or comparison may be automated so as to assist the user in more quickly reaching a confirmation of the identity of the drug sample.

It will be appreciated by those familiar with digital imaging technologies that such a system may require a standardized or controlled system for imaging and reviewing visual information. To assure some standardization in the data gathered, the present invention includes an imaging module 40 (discussed below in more detail), where the drug sample or specimen (e.g., pill) is placed on a specimen platen or platform, for illumination and imaging by a high resolution, color digital image capture device (e.g., digital camera, etc.).

Figure 2:
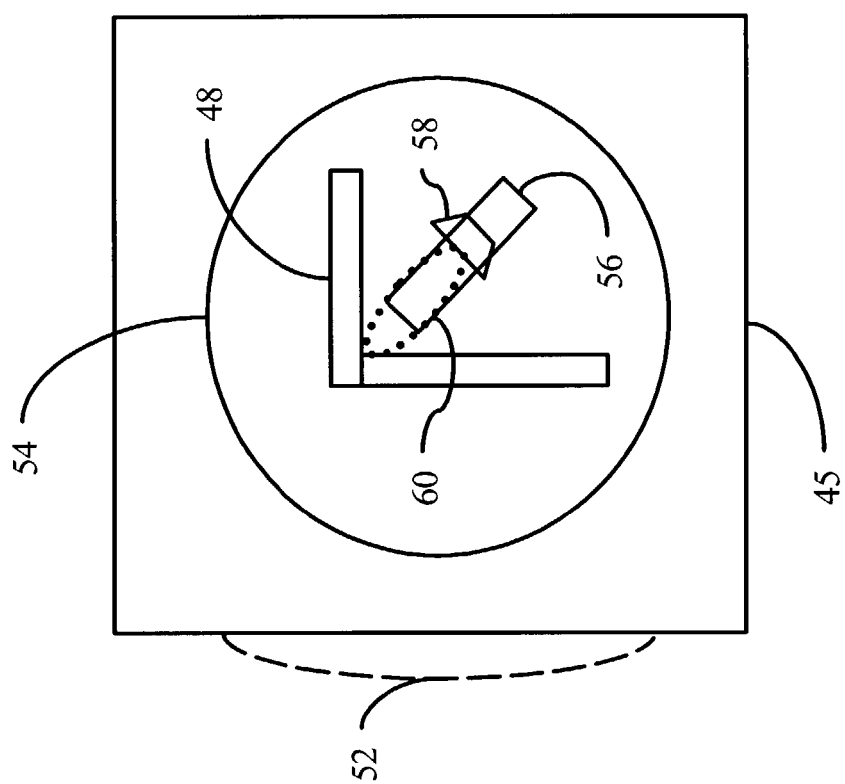
FIG. 2 is a top view example of the mounting platform for the imaging module of the present invention.

FIG. 2 illustrates, in more detail, certain components of the imaging module. As illustrated in FIG. 2, a mounting platform 45 includes a platen 54. The platen 54, in one embodiment of the present invention, can be optionally provided with a wheel 52 to enable the platen 54 to be rotated at least 90 degrees to enable imaging of the drug sample from various other perspectives.

There are preferably two detent points on the wheel 52 (not shown) that allow the user to select a position at 0 degrees or 90 degrees. The mounting platform 45 is mounted on rails (not shown) so that it can then be slide into and out of the imaging module.

Upon the platen 54, a backstop 48 and slide detent 58 are provided to secure the drug sample 60 upon the platen for proper imaging. The slide detent 58 slides along grove 56 and has a spring mounted lever (not shown) that holds it in place so as to secure the drug sample 60 against the backstop 48. The user is expected to slide the detent back, position the drug sample 60 against both sides of the backstop 48, and then slide the detent 58 forward so that it touches the drug sample 60 and holds it securely in place. The drug sample 60 is position on the platen 54 to enable a top perspective, a front perspective, and a side perspective of the drug sample 60 to be imaged simultaneously.

Figure 3:
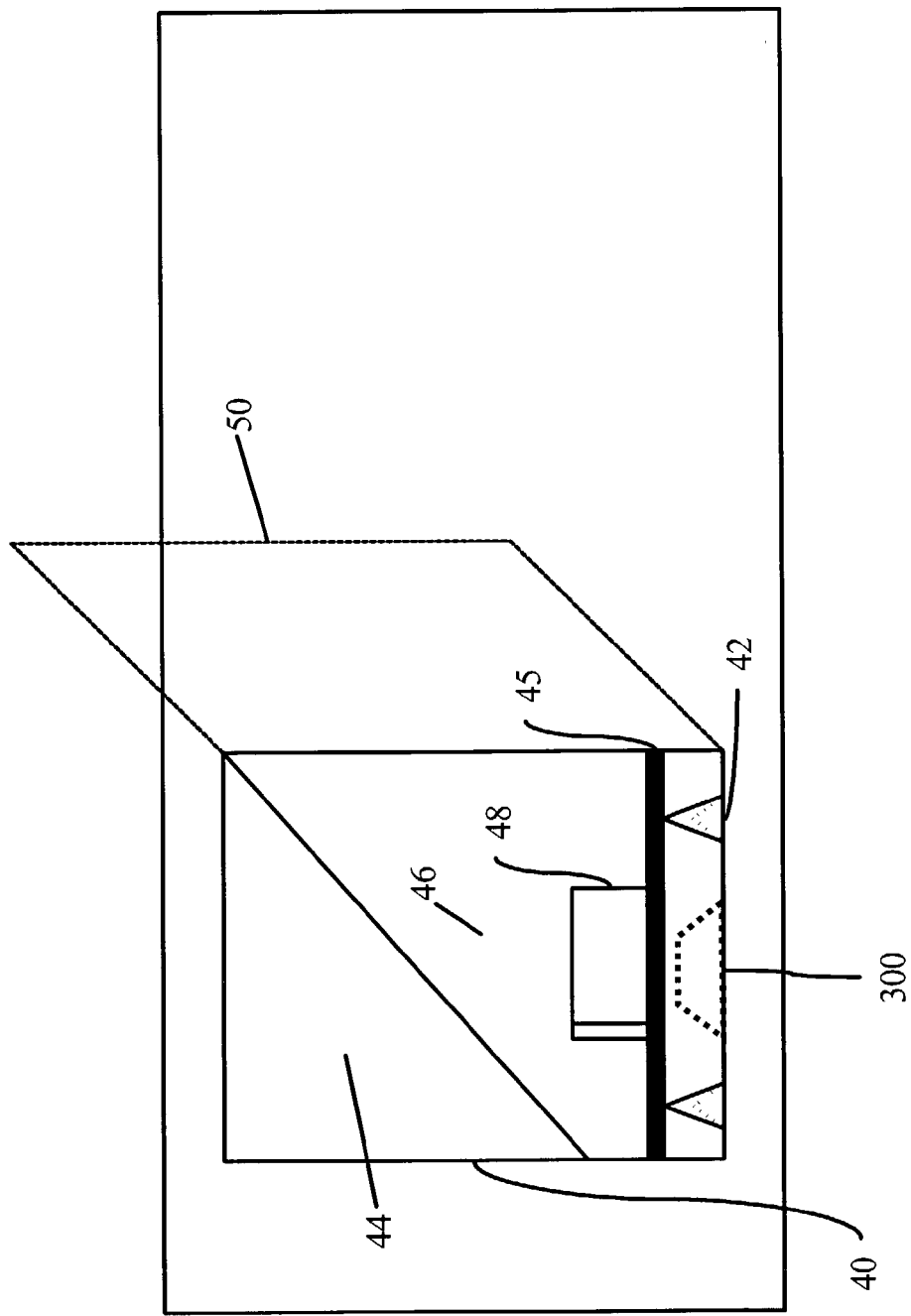
FIG. 3 is a side view example of a mounting platform within the imaging module of the present invention.

FIG. 3 illustrates the mounting platform 45 within the imaging module 40. As illustrated in FIG. 3, the mounting platform 45 has been slid into place in the imaging module 40. The drug sample is placed on the platen while the mounting module 45 is outside the imaging module 40. The mounting platform 45 can slide in and out of the imaging module 40 using either motorized means or manual means. A door 50 provides an opening into the imaging module 40 for the mounting platform 45 to enter.

Mounting members 42 secure the mounting platform 45 in the imaging module 40. The mounting members 42 provide stability to the mounting platform 45 and the correct position for proper imaging of the drug sample thereon.

In one embodiment of the present invention, a scale 300 is provided in the imaging module 40 under the mounting platform 45. The scale 300 can provide an accurate measurement of the weight of the drug sample being imaged prior to or after imaging. In this embodiment, the mounting members 42 retract to allow the mounting platform to rest upon the scale 300. Scale 300 measures the drug sample's weight and then the mounting members 42 lift the mounting platform 45 off the scale 300 and place the mounting platform 45 into its proper position for imaging.

As further illustrated in FIG. 3, the mounting platform 45 includes the backstop 48. The imaging module 40 includes a first reflective surface 44, such as a mirror, which enables a top view perspective of the drug sample to be imaged. The imaging module 40 also includes a second reflective surface 46, such as a mirror, which enables a side view perspective of the drug sample to be imaged. During imaging, the door 50 is closed. It is also noted that the platen 54 of FIG. 2 may be rotated while inside or outside the imaging module.

Figure 4:
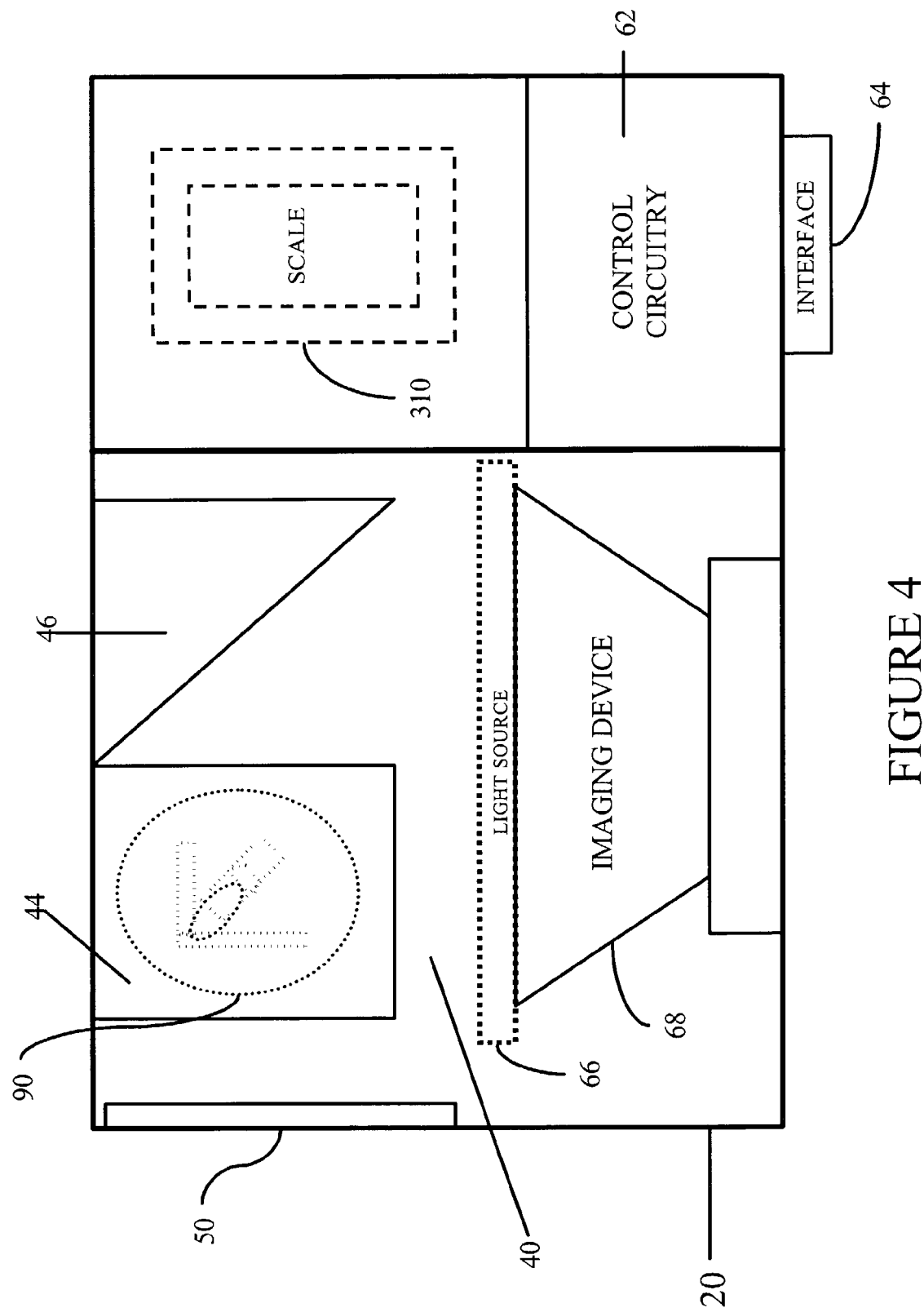
FIG. 4 is a block diagram of one embodiment of a drug sample ID peripheral according to the concepts of the present invention.

FIG. 4 illustrates one embodiment of the drug sample identification peripheral 20, according to the concepts of the present invention. It is noted that this embodiment may be designed to be portable. In this embodiment, the drug sample identification peripheral 20 includes an imaging module 40, a scale module 310, an interface 64, and a control circuitry module 62. It is noted that the scale for this embodiment can also be part of the mounting platform as illustrated in FIG. 3.

In the imaging module 40, a drug sample area 90, which includes the drug sample, backstop, platen, and slide indent, is to be imaged by an imaging device 68. The imaging device 68 may be a form of a digital camera, a CCD array, or other photosensitive imaging device that converts light energy into a digital representation of the image. The drug sample area 90 may be illuminated by a known light source 66, which may be a momentary flash or a continuous illumination source, having a spectrum sufficient or optimized to the imaging device. It is noted that the focal length of the imaging device 68 is such that the reflective surfaces 44 and 46 are positioned at that focal length to insure the highest quality imaging.

A door 50 is provided to allow the placing of the drug sample upon the platen and placing the mounting platform within the imaging module 40. The imaging module 40 may also include a color calibration strip (not shown) to enable calibration of the imaging device 68.

The imaging device 68 receives light reflected from reflective surface 44, which provides a top view perspective of the drug sample area 90, and reflective surface 46, which provides a side view perspective of the drug sample area 90. This enables the imaging device 68 to image two different perspectives, in addition to the front perspective, of the drug sample area 90 simultaneously. A portion of the imaging device 68 receives the top view perspective of the drug sample area 90, another portion of the imaging device 68 receives the side view perspective of the drug sample area 90, and a third portion of the imaging device 68 receives the front view perspective of the drug sample area 90. The actual size of the portion corresponds to the actual dimensions of the reflective surfaces 44 and 46.

The control circuitry module 62 may include a control board, central processing unit, or other control/logic unit to control the functions and operations of the imaging module 40, the scale 310, and the interface 64. The control circuitry module 62 may also include a memory, a power supply, and/or communication circuitry. The power supply may be a battery or rechargeable battery. The power supply may also include an AC to DC adapter. The control circuitry module 62 may also include image-processing applications or circuitry that can process the image data so as to provide a higher quality digital representation of the imaged drug sample.

The interface 64 may provide a port or ports for a parallel cable connection, a serial cable connection, a universal serial bus cable connection, an infrared connection, or a wireless connection to another computing device.

The physical characteristics that are preferably recorded by the drug sample identification peripheral 20 include weight (preferably in milligrams (accurate to +/−0.01 mg); size (in millimeters, accurate to +/−0.01 mm); height, width, depth, and shape type; color (e.g., RGB values or other colorimetric characteristics); and image (four views).

FIG. 5 illustrates another embodiment of the drug sample identification peripheral 20, according to the concepts of the present invention. It is noted that this embodiment may be designed to be portable. In this embodiment, the drug sample identification peripheral 20 includes an imaging module 40, a scale module 310, an interface 64, a control circuitry module 62, and a detachable digital camera unit 72. It is noted that the scale for this embodiment can also be part of the mounting platform as illustrated in FIG. 3.

In the imaging module 40, a drug sample area 90, which includes the drug sample, backstop, platen, and slide indent, is to be imaged by the detachable digital camera unit 72. The drug sample area 90 may be illuminated by a known light source 66, which may be a momentary flash or a continuous illumination source, having a spectrum sufficient or optimized to the detachable digital camera unit 72.

It is noted that the focal length of detachable digital camera unit 72 is such that the reflective surfaces 44 and 46 are positioned at that focal length to insure the highest quality imaging. To ensure proper positioning, stop members 70 are formed on the imaging module 40. The dimensions and shape of the stop members 70 are such that the lens of the detachable digital camera unit 72 snuggly fits within the imaging module 40 and the focal length of the detachable digital camera unit 72 corresponds to the reflective surfaces 44 and 46. The drug sample identification peripheral 20 may also include means (not shown) to temporarily attach the detachable digital camera unit 72 to the imaging module 40 securely.

A door 50 is provided to allow the placing of the drug sample upon the platen and placing the mounting platform within the imaging module 40. The imaging module 40 may also include a color calibration strip (not shown) to enable calibration of the detachable digital camera unit 72.

The detachable digital camera unit 72 receives light reflected from reflective surface 44, which provides a top view perspective of the drug sample area 90, and reflective surface 46, which provides a side view perspective of the drug sample area 90. This enables the detachable digital camera unit 72 to image two different perspectives of the drug sample area 90 simultaneously, in addition to the front view perspective of the drug sample area 90. A portion of the detachable digital camera unit 72 receives the top view perspective of the drug sample area 90, another portion of the detachable digital camera unit 72 receives the side view perspective of the drug sample area 90, and a third portion of the detachable digital camera unit 72 receives the front view perspective of the drug sample area 90. The actual size of the portion corresponds to the actual dimensions of the reflective surfaces 44 and 46.

The control circuitry module 62 may include a control board or processing unit to control the functions and operations of the imaging module 40, the scale 310, and the interface 64. The control circuitry module 62 may also include a memory, a power supply, and/or communication circuitry. The power supply may be a battery or rechargeable battery. The power supply may also include an AC to DC adapter. The control circuitry module 62 may also include image-processing applications or circuitry that can process the image data so as to provide a higher quality digital representation of the imaged drug sample.

Lastly, the control circuitry module 62 may include communication circuitry, which allows the detachable digital camera unit 72 to transfer image data, via a cable 74, to the control circuitry module 62. The communication circuitry enables an efficient transfer of image data and mass data from the drug sample identification peripheral 20 to another computing device over a single cable or communication channel.

The interface 64 may provide a port or ports for a parallel cable connection, a serial cable connection, a universal serial bus cable connection, an infrared connection, or a wireless connection to another computing device.

The physical characteristics that are preferably recorded by the drug sample identification peripheral 20 include weight (preferably in milligrams (accurate to +/−0.01 mg); size (in millimeters, accurate to +/−0.01 mm); height, width, depth, and shape type; color (e.g., RGB values or other colorimetric characteristics); and image (multiple views).

One aspect of the present invention contemplates a system for cross-referenced access to image and knowledge databases for the purpose of assisting in the identification of street drugs. The systems, as described above, would automatically transfer the above-described physical characteristics recorded by the drug sample identification peripheral to a computing device that would include a diagnostic engine that could identify, from a plurality of possible street drugs, a subset of street drugs that are consistent with the characteristics.

Optionally, the systems could also include a user-interface to solicit a plurality of additional characteristics of a sample. For example these additional characteristics might include the form of the drug (powder, capsule, tablet, liquid, patch, gaseous), method of administration (if known) (oral, injection, epidermal, smoking/inhalation), markings, geographic location of use, drug user's symptoms, primary chemical composition (determined through commonly used drug tests employed by police officers, such as the Marquis Test, Mandelins Test and the Liebermans Test).

Furthermore, based upon the characteristics indicated by a user and the physical characteristics provided by the drug sample identification peripheral, a diagnostic engine would then identify, from a plurality of possible street drugs, a subset of street drugs that are consistent with the characteristics. Using the subset of street drugs, an information space of the image database could then be sorted for presentation to the user, wherein the presentation is accomplished through the concurrent presentation of a plurality of images for user review in the identification of the street drug.

In the case of street drugs such as pills, it is further contemplated that such images would be of a standard size, imaged against a defined background (in the case of pills), perhaps including a grid imprinted thereon to aid a viewer in assessing the size of the pill. This standard-reference image would then have the pill represented uniformly so that the user could have an immediate standard visual reference for comparison. Textual information regarding product or chemical name or ingredients, symptoms, treatments (if any), and additional tests to identify substance, would also appear in response to the user's selections on the interface screen.

In addition, a second aspect of the embodiments, described above, is to prospectively collect information from users of the present invention to augment the database (street drug appearances are changing all the time). Use of the present invention would assure that the set of users (forensic chemists or other crime lab personnel, drug enforcement investigators, other public safety or police personnel) would have an imaging terminal/station creating a standard set of images for image acquisition (standard grid, lighting, backdrop, item position on grid, and distance from object). Subsequently, images acquired using the system or method would then be sent electronically to a centralized image database, along with additional characteristic details (weight (mg), size (mm), laboratory analysis results, date item received, number of items seized, location, product name, listed contents (from label if in a container), possibly received from other input devices. The centralized database would also be a searchable database (with the addition of searching and display of geography, to follow the spread of specific drugs from locale to locale, for instance).

It is anticipated that the present invention may be used by field personnel as well as lab personnel and should, therefore, be easy to set up and use. A typical sequence of use of the present invention is as follows. Initially the sample tray is opened and the sample is placed in the tray and closed so that the sample is positioned in the imaging module. The physical characteristics of the sample are recorded by software, a selected recording mode option, or the peripheral using application software. The sample is rotated and recorded again.

It will be further appreciated that use of the system may require calibration of the system. A reference sample will be included with the imaging module as noted above. A typical calibration procedure inserts reference sample into imaging module; record measurement; select calibration mode; input correction required for reading to equal known reference value; repeat for consistency; and repeat for all measurement categories.

The following description characterizes one possible scenario in which the present invention may be used. The scenario is intended for purposes of illustrating the advantages of the present invention and is not intended to limit the particular applications or embodiments of the present invention.

The drug sample identification system may be located in a police vehicle and used by the patrol officer, or brought to the scene of a suspected situation by a field technician/investigator. In either case, the officer would set up the system and put it to use. This procedure may include entering information such as officer name & number, location of event, date & time, etc.; placing a weight calibration reference on the scale and recording weight; placing an imaging calibration reference in imaging module, recording a picture, rotating, and recording second picture; recording calibration information; placing suspected substance on scale and recording weight; placing suspected substance in imaging module, recording a picture, rotating, and recording another picture; displaying the generated characteristics; searching a database using these characteristics; optionally, performing additional searches; based upon the information and images, make a determination whether to charge the suspect; if the suspect is charged, save all information as an incident report; saving a "new drug" set of information, that can be uploaded to a centralized main database; and periodically checking for database updates by either downloading from the central main system, or installing from a removable storage media.

One aspect of the invention deals with a basic problem in the collection of data and identification of drug samples—the delay in time and standardization of data about drug samples. This aspect is further based on the discovery of a technique that alleviates this problem. The technique recognizes the advantage of using standardized, and portable data collection equipment to assist in the characterization and recording of physical information, including visual images, of drug samples at crime scenes, in emergency rooms, etc.

The present invention, as described above, provides both a simple and inexpensive means for providing a standardized input to a drug sample database compared to other approaches. As a result, legal and medical professionals will be able to access and provide drug sample information so as to enable the trafficking and distribution of drugs to be better monitored and controlled.

In summary, the present invention is a drug sample identification system, including a scale for weighing a drug sample and an imaging module for capturing digital images of the drug sample, from at least two different visual perspectives, and an transmitting the collected data and images, via an interface, to a computer for storage and association with a software program and image database.

It is, therefore, apparent that there has been provided, in accordance with the present invention, a method and apparatus to assist with the identification of oral pharmaceuticals such as pills, and including illegal street drugs.

While various examples and embodiments of the present invention have been shown and described, it will be appreciated by those skilled in the art that the spirit and scope of the present invention are not limited to the specific description and drawings herein, but extend to various modifications and changes all as set forth in the following claims.

What is claimed is:

1. A drug sample identification system, comprising:
    an imaging staging module to enable substantially simultaneous image capturing of a first perspective view of a drug sample, a second perspective view of the drug sample, and a third perspective view of the drug sample, the first perspective view of the drug sample being different from the second perspective view of the drug sample, the first perspective view of the drug sample being different from the third perspective view of the drug sample, the second perspective view of the drug sample being different from the third perspective view of the drug sample, the first perspective view of the drug sample being orthogonal to the third perspective view of the drug sample, the second perspective view of the drug sample being orthogonal to the third perspective view of the drug sample.

2. The drug sample identification system as claimed in claim 1, further comprising:
    a digital imaging device to generate a digital image of the drug sample located in said imaging staging module, said digital image representing an image of the drug sample from the first, second, and third perspective views of the drug sample.

3. The drug sample identification system as claimed in claim 1, further comprising:
    a scale to weigh a drug sample.

4. The drug sample identification system as claimed in claim 2, further comprising:
    an interface to enable a transmission of drug sample data including said digital image of the drug sample located in said imaging staging module to another electronic device for storage and association with a database.

5. The drug sample identification system as claimed in claim 3, further comprising:
    an interface to enable a transmission of drug sample data including the weight of the drug sample and said digital image of the drug sample located in said imaging staging module to another electronic device for storage and association with a database.

6. The drug sample identification system as claimed in claim 1, further comprising:
    a digital imaging mounting device to enable an external digital imaging device to be mounted so as to generate images from drug samples located in said imaging staging module.

7. The drug sample identification system as claimed in claim 1, wherein said imaging staging module comprises:
    a staging device to position the drug sample for imaging;
    a first reflective surface to provide the first perspective view of the drug sample positioned in said imaging staging module; and
    a second reflective surface to provide the second perspective view of the drug sample positioned in said imaging staging module;
    said first and second reflective surfaces being positioned to enable image capturing of the drug sample from the first, second, and third perspective views substantially simultaneously.

8. The drug sample identification system as claimed in claim 2, wherein said imaging staging module comprises:
    a staging device to position the drug sample for imaging;
    a first reflective surface to provide the first perspective view of the drug sample positioned in said imaging staging module; and
    a second reflective surface to provide the second perspective view of the drug sample positioned in said imaging staging module;
    said first and second reflective surfaces being positioned to enable image capturing of the drug sample from the first, second, and third perspective views substantially simultaneously.

9. The drug sample identification system as claimed in claim 7, wherein said staging device comprises:
    a planar member to position the drug sample thereupon;
    first and second backing members oriented at an angle therebetween to contact the drug sample at least two points; and
    a movable member, opposed to said first and second backing members, to provide a third contact point to hold the drug sample in a fixed position on said planar member.

10. The drug sample identification system as claimed in claim 8, wherein said staging device comprises:
    a planar member to position the drug sample thereupon;
    first and second backing members oriented at an angle therebetween to contact the drug sample at least two points; and
    a movable member, opposed to said first and second backing members, to provide a third contact point to hold the drug sample in a fixed position on said planar member.

11. The drug sample identification system as claimed in claim 7, wherein said imaging staging module further comprising:
    a sliding mechanism to move said staging device from an imaging position to a loading position.

12. The drug sample identification system as claimed in claim 8, wherein said imaging staging module further comprising:
    a sliding mechanism to move said staging device from an imaging position to a loading position.

13. The drug sample identification system as claimed in claim 7, wherein said staging device is rotatable such that an orientation of the drug sample may be altered by a user when the drug sample is in an imaging position.

14. The drug sample identification system as claimed in claim 8, wherein said staging device is rotatable such that an orientation of the drug sample may be altered by a user when the drug sample is in an imaging position.

15. The drug sample identification system as claimed in claim 4, wherein said interface provides hardwire communication of the drug sample data including the weight of the drug sample and said digital image of the drug sample located in said imaging staging module to another electronic device for storage and association with a database.

16. The drug sample identification system as claimed in claim 2, further comprising:
 a display to provide a visualization of the imaged drug sample and to provide a visualization of known drugs from a database;
 said display displaying information for a user; and
 an input device to enable a user to control a functionality for the drug sample identification system and to input information related to the drug sample.

17. The drug sample identification system as claimed in claim 9, wherein said planar member including a scale device to weigh the drug sample.

18. The drug sample identification system as claimed in claim 10, wherein said planar member including a scale device to weigh the drug sample.

19. A method for identifying a drug sample, comprising:
 (a) placing a drug sample in an imaging stage module; and
 (b) image capturing, substantially simultaneously, a first perspective view of a drug sample, a second perspective view of the drug sample, and a third perspective view of the drug sample, the first perspective view of the drug sample being different from the second perspective view of the drug sample, the first perspective view of the drug sample being different from the third perspective view of the drug sample, the second perspective view of the drug sample being different from the third perspective view of the drug sample, the first perspective view of the drug sample being orthogonal to the third perspective view of the drug sample, the second perspective view of the drug sample being orthogonal to the third perspective view of the drug sample.

20. The method as claimed in claim 19, further comprising:
 (c) weighing the drug sample; and
 (d) transmitting the captured image of the drug sample and the weight of the drug sample to another electronic device for storage and association with a database.

21. A drug sample identification system, comprising:
 an imaging staging module to provide, at a single image plane, a first perspective view of a drug sample, a second perspective view of the drug sample, and a third perspective view of the drug sample so as to enable substantially simultaneous image capture of first, second, and third perspective views of the drug sample at said single image plane, the first perspective view of the drug sample being different from the second perspective view of the drug sample, the first perspective view of the drug sample being different from the third perspective view of the drug sample, the second perspective view of the drug sample being different from the third perspective view of the drug sample, the first perspective view of the drug sample being orthogonal to the third perspective view of the drug sample, the second perspective view of the drug sample being orthogonal to the third perspective view of the drug sample.

* * * * *